United States Patent
Kohls

(10) Patent No.: US 6,520,910 B1
(45) Date of Patent: Feb. 18, 2003

(54) METHOD AND SYSTEM OF ENCODING PHYSIOLOGICAL DATA

(75) Inventor: Mark Robert Kohls, New Berlin, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 0 days.

(21) Appl. No.: 09/688,299

(22) Filed: Oct. 13, 2000

(51) Int. Cl.[7] .......................... A61B 5/00; A61B 10/00; G06K 9/36

(52) U.S. Cl. ................ 600/300; 600/509; 382/232; 128/922

(58) Field of Search .................. 607/32, 60, 9; 600/300, 301, 515, 509, 407; 128/920–925, 903, 904; 382/128–134, 232–253; 345/733; 348/77

(56) References Cited

U.S. PATENT DOCUMENTS

| | | | |
|---|---|---|---|
| 4,633,884 A | | 1/1987 | Imai et al. |
| 5,515,176 A | * | 5/1996 | Galen et al. ............. 128/904 |
| 5,619,995 A | * | 4/1997 | Lobodzinski ............. 600/301 |
| 5,623,935 A | | 4/1997 | Faisandier |
| 5,836,982 A | * | 11/1998 | Muhlenberg et al. ...... 600/515 |
| 5,838,823 A | * | 11/1998 | Ancessi .................. 382/232 |
| 5,912,656 A | * | 6/1999 | Tham et al. ............. 600/300 |
| 5,920,317 A | * | 7/1999 | McDonald ................ 600/407 |
| 6,115,486 A | * | 9/2000 | Cantoni .................. 382/128 |
| 6,281,893 B1 | * | 8/2001 | Goldstein ................ 345/733 |

OTHER PUBLICATIONS

Andres, Clay, Integrating Multimedia into the the Structure, 1999, IDG Books Worldwide, Inc. Chapter 6, p. 1.*

* cited by examiner

Primary Examiner—Max F. Hindenburg
Assistant Examiner—David J. McCrosky
(74) Attorney, Agent, or Firm—Michael Best & Friedrich LLP

(57) ABSTRACT

A method and system of encoding physiological data. In one embodiment of the invention, raw data is transformed into formatted images and then the formatted images are encoded. The data is transferred at full resolution once to a main server and then the superimposition of the data is encoded using a compression scheme. Preferably, the data is encoded using difference-based encoding, such as MPEG encoding. Encoding the data in this way makes it possible to perform data analysis on a wide variety of workstations, not just high-performance machines.

26 Claims, 3 Drawing Sheets

METHOD AND SYSTEM OF ENCODING PHYSIOLOGICAL DATA

BACKGROUND OF THE INVENTION

The present invention relates to methods and devices used to review and record physiological data, such as blood pressure and electrocardiogram data. More particularly, the invention relates to a method and a system of reducing the amount of physiological data delivered to devices used to review and analyze the data, thereby reducing the complexity of and resources required in those devices.

Modern medical practice involves monitoring a variety of physiological activity. In electrocardiography and other types of patient monitoring, current data is often compared to historical data in order to observe the trends and changes in the data. As can be appreciated, the amount of data collected in monitoring activities can be very large. For example, in ambulatory ECG monitoring, changes in QRS waves are identified by visually comparing current and previous measurements. With current technology, the QRS data must be stored locally at a computer or workstation. The amount of data acquired is generally on the order of 40MB or more. The amount of time required to transfer this amount of data from the acquisition device to the analysis workstation makes historical comparisons impractical, except with very fast (and, therefore, expensive) data links and high performance workstations.

In addition to the data volume problem noted above, another deficiency with many current monitoring techniques is that the review and analysis device must process raw data and have appropriate software sophisticated enough to display the data. Data from physiological monitoring devices is typically transferred in a raw fonnat, i.e., the actual sample points from the A-to-D converters or filtered A-to D values. This technique requires any computer that displays the information to understand the raw data format. Generally, only very powerful workstations and computers with a complete set of programs are able to process raw data. Thus, many present systems used to analyze data are relatively expensive.

SUMMARY OF THE INVENTION

Accordingly, it would be desirable to have a method and system for reducing the amount of data handled by analysis devices to reduce the complexity of and resources required by those devices.

The invention provides a method and system that formats physiological data before transmission to a monitoring device using, encoding or streaming techniques to reduce the volume of the data, thereby reducing the need to have sophisticated monitoring devices. The invention may be used in several monitoring applications such as ambulatory or walking ECG monitoring (a/k/a Holter monitoring). In ambulatory ECG applications data is usually reviewed by superimposing current and previous QRS complex data to identify changes over time. In one embodiment of the invention, data is transferred at full resolution once to a main server and then the superimposition of the data is encoded using MPEG compression. The MPEG image of the data is substantially smaller yet offers the same degree of functionality since the MPEG image stream to the reviewer looks the same as the superimposition of the raw data. This improvement also uses fewer computing resources for playback. This is also applicable to full disclosure review for Holter monitoring.

The invention is also applicable to 12 or 15-lead ECG data monitoring. Raw sensor data is transformed into formatted images and then the formatted images are encoded as an MPEG video stream. The formatting and encoding condenses a very large amount of data into a very small data set that can be easily displayed on any computer. The invention also takes advantage of frame-by-frame review of the image supported by the MPEG format to permit the clinician to view changes in the ECG over time.

Yet another application of the invention involves generating a continuous display of waveforms. In this embodiment of the invention, data is encoded as a stream of digital video and/or audio depending on the type of raw signal. Preferably, the data is encoded using difference-based encoding, such as MPEG encoding. Encoding the data in this way makes it possible to perform data analysis on a wide variety of workstations, not just high-performance machines.

As is apparent from the above, it is an advantage of the present invention to provide a method and system of encoding physiological data to reduce the amount of data processed by analysis devices. Other features and advantages of the present invention will become apparent by consideration of the detailed description and accompanying drawings.

DETAILED DESCRIPTION

Figure 1:
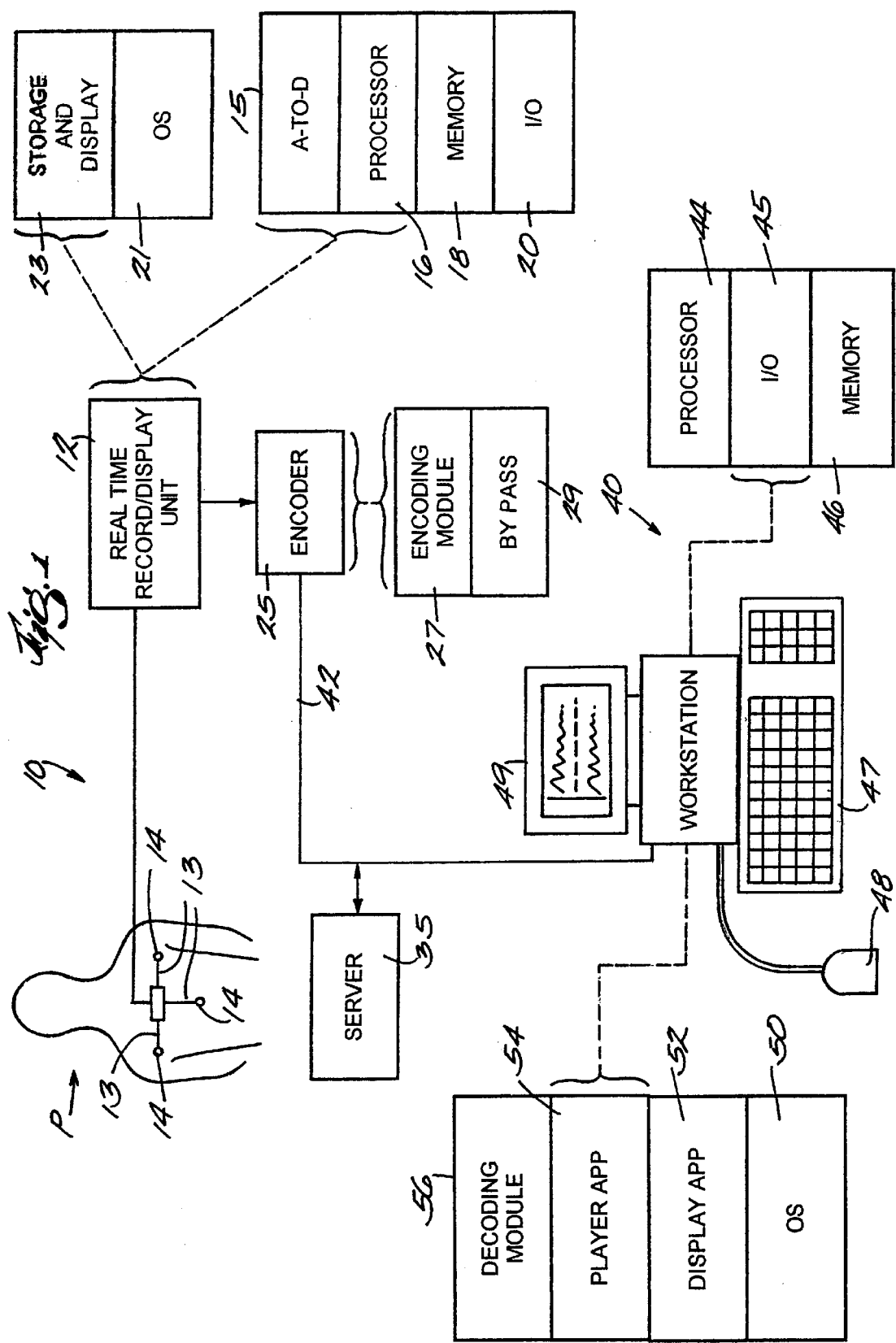
FIG. 1 is a schematic drawing of an apparatus embodying the invention.

Before one embodiment of the invention is explained in detail, it is to be understood that the invention is not limited in its application to the details of the construction and the arrangements of the components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

FIG. 1 illustrates a system 10 for acquiring and reviewing physiological data, such as ECG and pressure waveforms, that embodies the invention. The system 10 includes a record/display unit 12 that, in the usual application, is externally connected to the patient through leadwires 13 and electrodes or sensors 14 attached to the skin of a patient P. The invention, however, is equally applicable to physiological data that is acquired in other ways, e.g., through electrodes placed directly on the heart, through transesophageal monitoring, through pressure sensors, etc.

The record/display unit 12 is equipped with an analog-to-digital (A-to-D) converter 15, a processor 16, a storage device or memory 18, and I/O interfaces 20. The record display unit 12 also includes an operating system 21, and storage and display software 23. Conventional record/display units including those sold under the trademark SEER by GE Medical Systems are suitable for use in the invention.

One function of the record/display unit 12 is to provide a local real-time display of the physiological data being received from the patient P. Another function of the record/ display unit 12 is to convert analog data from the sensors coupled to the patient P to a digital format.

Digital data from the record/display unit 12 is delivered to difference-based encoder 25. The encoder 25 has an encoding module 27 and a by-pass link 29, which may be chosen to pass raw digitized data directly from the record/display unit 12 to a server 35 and/or analyzer work station 40 over a communication link 42. The encoder 25 may be located on the server 35 or may be positioned locally with the record/display unit 12, as shown. The workstation 40 includes typical hardware such as a processor 44, I/O interfaces 45, and storage devices or memory 46. The workstation may also include input devices such as a keyboard 47 and a mouse 48. The workstation may also include standard output devices, such as a monitor 49.

On the software side the workstation includes an operating system 50, a display application 52, a player application 54, and a decoding module 56. While shown separately, the player application 54 and decoding module 56 can be combined in a single functional unit.

Data is collected from the patient P by the record/display unit 12. The record/display unit 12 takes the analog data from the sensors 14 and converts that data into a digital form, which is often referred to as raw data. That is, data that has merely been passed through an analog-to-digital ("A-to-D") converter or perhaps passed through an A-to-D converter and some filters. The record/display unit 12 also provides a mechanism to display the data locally at the patient location. The recorded data from the record/display unit 12 is then transferred to the encoder 25. As noted, the encoder 25 may be located locally with the record/display unit 12 or positioned at a server 35. In those instances where it is important to conduct a superimposition analysis, the raw data is transferred once, at full resolution, to either the server 35 or the workstation 40. The by-pass,29 of the encoder 25 is used to permit the transfer of raw data from the record/display unit 12 to the server 35 or workstation 40. The superimposition data is then encoded (as described below) using the encoder 25.

Regardless of its exact location, the encoder 25 encodes the superimposition data (or data subsequent to the base or first raw data set) sent to the server 35 or workstation 40. In one embodiment, the superimposition is encoded using a difference-based codec (compressor-decompressor) algorithm. Suitable codec algorithms include the MPEG-family of methodologies. As is known, MPEG works on encoding the difference from one frame of data to the next. The first frame of the data stream is used to encode a base or "key frame." Generally, very little information changes from one frame to the next in a video presentation. So, an MPEG encoder only stores the differences from one frame to the next, resulting in a large reduction in file size and storage requirements.

Figure 2:
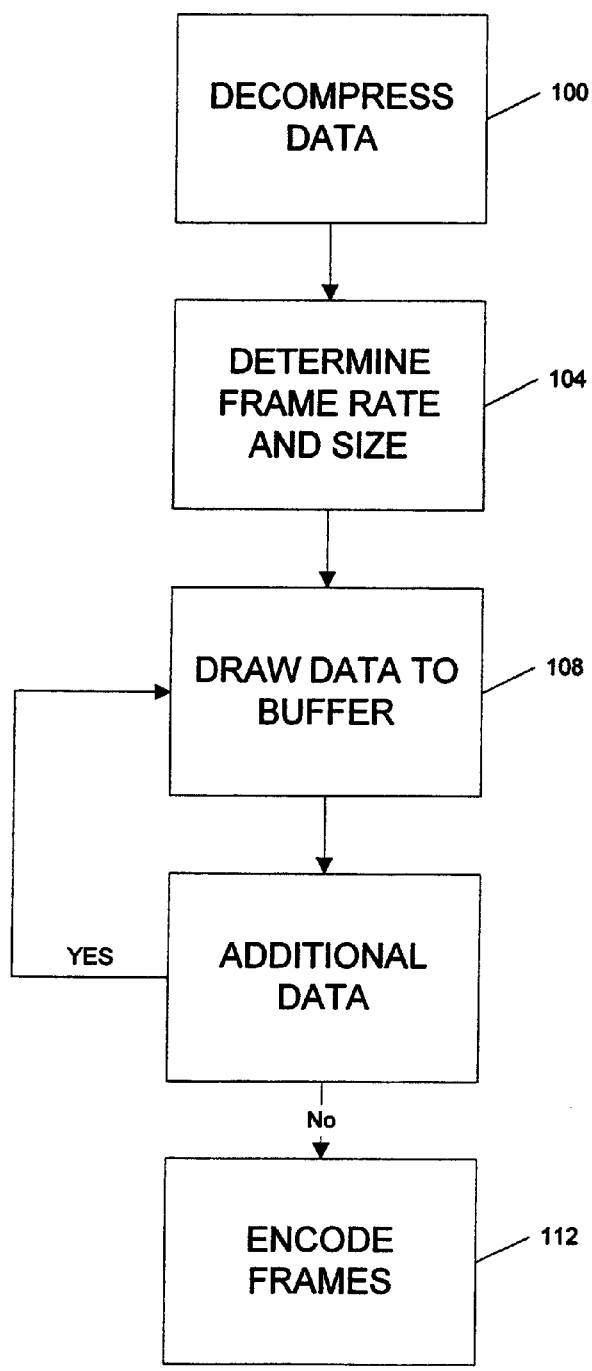
FIG. 2 is a flow chart of an encoding methodology used in the invention.

While MPEG methodologies are normally applied to video information, the inventor has determined a way to use such methodologies with physiological data. As implemented in the invention, the superimposition data, in its raw form from the record/display unit 12 (a first data set) is sent to the encoder 25. As shown in FIG. 2, the encoder 25 then decompresses the raw data, if necessary, at step 100. The recording device may have compressed the raw data to economize on the amount of storage required in the device. In order to convert the physiological data to a videolike form, the encoder determines a frame rate (in frames per second) and a frame size (the amount of information in each frame) for the physiological data, as shown at step 104. The encoder then begins creating individual frames of data. As shown in step 108, the encoder draws chunks or pieces of data into a frame buffer. Data is drawn into the frame buffer for each physiological event, such as a QRS complex, that occurs in the time allocated for a single frame. The number of physiological events per frame will vary depending on the frame rate chosen for display. Step 108 is repeated until all of the data is drawn into successive frames. When all the data is drawn into frames, a second data set or video or "movie" version of the superimposition data is created. The second data set is then encoded at step 112 using a difference-based encoder, such as an MPEG encoder or other suitable codec. MPEG-1, MPEG-2, and MPEG-4 encoders are appropriate, but other difference based codecs could be used.

With the invention, it is not necessary to postpone encoding the data until the entire movie or second data set has been created. Individual frames may be encoded after they are created, and then the encoded frames can be compiled or transferred. All that is required is that the MPEG encoder be at least one frame behind the raw data converter.

In addition to difference based encoding, a vector graphics algorithm may be used to encode the superimposition data. A vector graphics algorithm inserts commands or "tags" into the data. A player on the workstation 40, such as the player application 54 reads tags and draws the screen (or printed page) based on interpreting the tags. Typically, the tags consist of instructions to set a drawing context, i.e., the height and width of the area to be displayed, instructions to draw text at particular coordinates in particular fonts, and other similar instructions. The tags include a set of "moveto" and "lineto" commands, or their equivalents. A "moveto" command instructs the player to move the drawing pen to a particular coordinate in the drawing plane. A "lineto" command instructs the player to draw a line from the pen's current position to the next position specified in the command. The tags may also include a "relative command" that instructs the player that the end position of the line is relative to the current position of the pen. Since the relative position of two points in a given physiological signal tends to be quite small, the technique tends to produce a highly reduced-size set of data that can still reproduce an image of the original signal.

Another benefit of vector graphics encoding is that the player typically antialiases drawing lines, resulting in smooth lines that are preferred for viewing physiological signals. The apparent resolution is boosted to the viewer without the need to send large amounts of raw data or to use high-resolution displays.

A third benefit of vector graphics encoding is that such encoding permits a snapshot to be created that contains all of the waveform data for a given time period. Such a snapshot may be saved and stored for replay without the use of an expensive special purpose workstation or computer.

Figure 3:
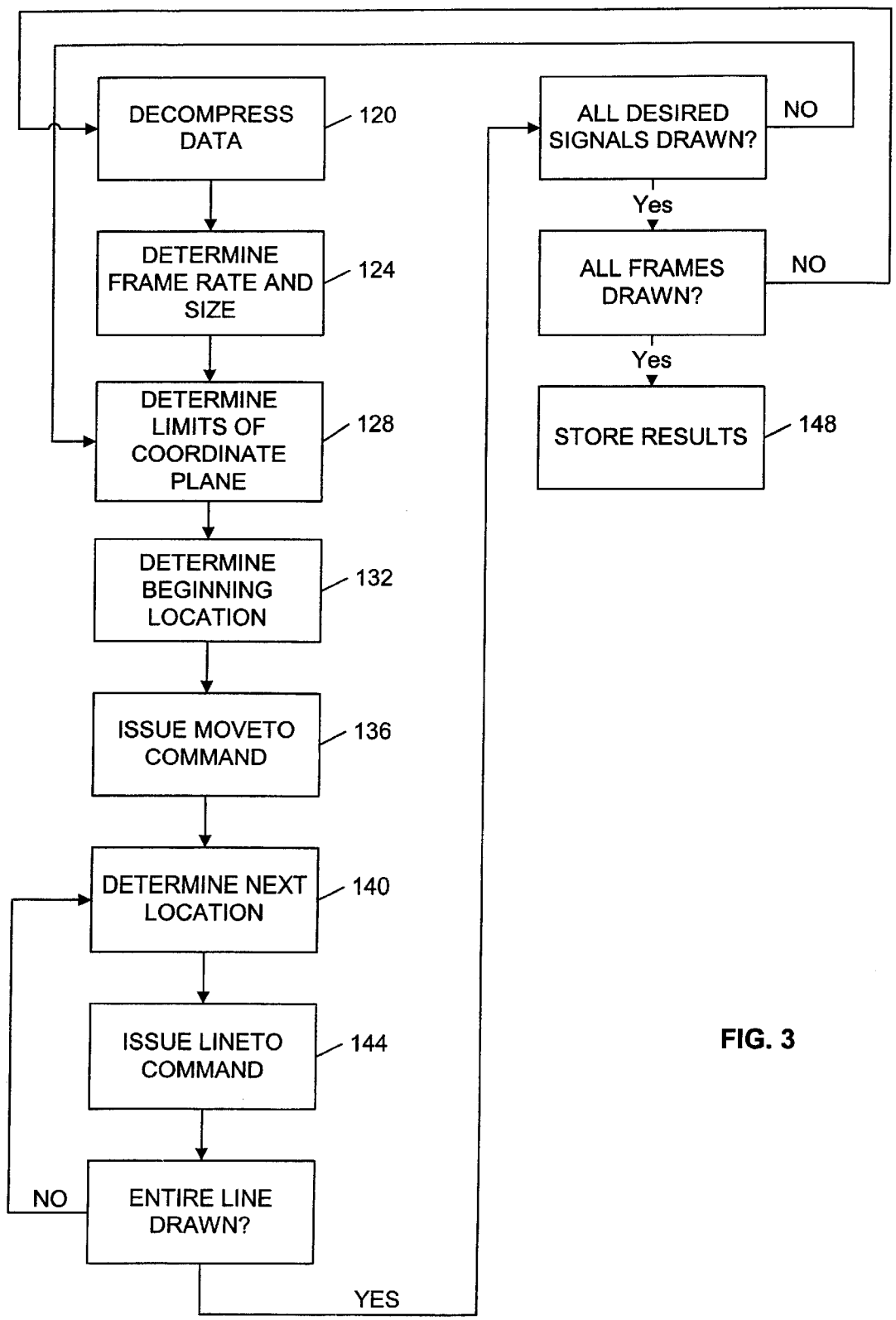
FIG. 3 is a flow chart of a second encoding methodology used in the invention.

When vector graphics encoding is used, the superimposition data, in its raw form from the record/display unit 12 (a first data set) is sent to the encoder 25. As shown in FIG. 3, the encoder 25 then decompresses the raw data, if necessary, at step 120. A frame rate and a frame size are then determined at step 124. The limits of a coordinate plane are then set at step 128 and a beginning location, in X-Y coordinates, for where to start drawing a waveform is then determined at step 132. A "moveto" command is then issued to the beginning location in the plane, as shown at step 136. The next point or location in the image is determined at step 140, and a "lineto" command is issued at step 144 to instruct the player to draw a line to the next set of coordinates. The coordinates could be relative or absolute coordinates, but relative coordinates are preferred since their use results in smaller files. Steps 140 and 144 are repeated until an entire line is drawn. Steps 128 through 144 are then repeated until all desired signals are drawn for a given frame. Steps 120 through 144 are then repeated until all desired frames are drawn for a given time period. Finally, as shown at step 148, the results are saved to storage (e.g. a secondary storage device) or transmitted to the server 35 or workstation 40. Although not shown, transmission could be done on a frame-by-frame basis rather than after the entire sequence is created.

As can be seen from the above, the invention provides a method and system for encoding physiological data.

Various features and advantages of the invention are set forth in the following claims.

What is claimed is:

1. A method of encoding physiological data, the method comprising:

acquiring non-image diagnostic data from a patient;

preprocessing the data to transform it to a video stream;

encoding the video stream to compress the preprocessed data;

transferring the encoded data to an analysis device; and processing the encoded data to generate an output.

2. A method as claimed in claim 1, wherein the data is encoded using a difference-based encoding scheme.

3. A method as claimed in claim 2, wherein the difference-based encoding scheme is an MPEG encoding scheme.

4. A method as claimed in claim 1, wherein the data is encoded using a vector-graphics encoding scheme.

5. A method as claimed in claim 1, wherein preprocessing the data includes decompressing the data.

6. A method of encoding physiological data, the method comprising:

acquiring non-image diagnostic data from a patient;

preprocessing the data to transform it to a video stream and determining a frame rate and a frame size;

encoding the video stream to compress the preprocessed data;

transferring the encoded data to an analysis device; and processing the encoded data to generate an output.

7. A method as claimed in claim 6, wherein preprocessing the data includes creating a plurality of frames of data.

8. A method as claimed in claim 7, wherein each frame is created by drawing data into a frame buffer for each physiological event that occurs in one frame.

9. A method as claimed in claim 8, wherein encoding the data includes encoding each frame independently after it is created.

10. A method of encoding physiological data, the method comprising:

acquiring non-image diagnostic data from a patient;

preprocessing the data to transform it to a video stream;

encoding the video stream to compress the preprocessed data using a vector-graphics based encoding scheme;

transferring the encoded data to an analysis device; and processing the encoded data to generate an output.

11. A method as claimed in claim 10, further comprising decompressing the data.

12. A method of encoding physiological data, the method comprising:

acquiring non-image diagnostic data from a patient;

preprocessing the data to transform it to a video stream;

determining a frame rate and a frame size;

encoding the video stream to compress the preprocessed data using a vector-graphics based encoding scheme;

transferring the encoded data to an analysis device; and processing the encoded data to generate an output.

13. A method as claimed in claim 12, further comprising determining limits of a coordinate plane.

14. A method as claimed in claim 13, further comprising determining a beginning location, in X-Y coordinates, for where to start drawing a waveform.

15. A method as claimed in claim 14, further comprising issuing a moveto command to the beginning location in the plane.

16. A method as claimed in claim 15, further comprising determining a second location and issuing a lineto command to instruct a player to draw a line to the second location.

17. A physiological data review system comprising:

a record and display unit capable of being coupled to a patient to acquire non-image diagnostic data;

an encoder coupled to the record and display unit and operable to convert the data to a video stream and to compress the data; and a workstation coupled to the encoder.

18. A system as claimed in claim 17, wherein the encoder includes an encoding module and a bypass.

19. A system as claimed claim 17, wherein the encoder includes a difference-based encoding module.

20. A system as claimed in claim 17, wherein the encoder includes a vector-graphics encoding module.

21. A system as claimed in claim 17, wherein the encoder determines a frame rate and a frame size.

22. A system as claimed in claim 17, further comprising a server and wherein the encoder is located on the server.

23. A system as claimed in claim 17, wherein the workstation includes a layer application.

24. A system as claimed in claim 17, wherein the workstation includes a decoding module.

25. A physiological data review system comprising:

a record and display unit capable of being coupled to a patient to receive non-image diagnostic data;

an encoder coupled to the record and display unit and operable to convert the data to a video stream and to compress the data, the encoder determining a frame rate and a frame size and drawing chunks of data into a frame buffer for each physiological event that occurs in one frame; and a workstation coupled to the encoder.

26. A method of analyzing physiological data comprising:

providing an acquisition and storage device;

acquiring and storing a first set of non-image diagnostic data and a second set of non-image diagnostic data;

formatting the first and second sets of non-image diagnostic data into sequential frames of a video stream;

encoding to compress the video stream; and transmitting the encoded video stream to a remote computing device.

* * * * *